United States Patent
Peruzzo et al.

(10) Patent No.: US 9,011,389 B2
(45) Date of Patent: Apr. 21, 2015

(54) SUPPORTING SLEEVE FOR A CONTAINER WITH A FLANGE

(75) Inventors: Grégory Peruzzo, Prunières (FR); Romain Lanier, Grenoble (FR); Adrien Plouvier, Saint Martin d'Heres (FR)

(73) Assignee: Becton Dickinson France, Le Pont de Claix (FR)

( * ) Notice: Subject to any disclaimer, the term of this patent is extended or adjusted under 35 U.S.C. 154(b) by 233 days.

(21) Appl. No.: 13/318,826

(22) PCT Filed: May 7, 2009

(86) PCT No.: PCT/IB2009/005933
§ 371 (c)(1),
(2), (4) Date: Jan. 18, 2012

(87) PCT Pub. No.: WO2010/128350
PCT Pub. Date: Nov. 11, 2010

(65) Prior Publication Data
US 2012/0123348 A1  May 17, 2012

(51) Int. Cl.
*A61M 5/32*  (2006.01)
(52) U.S. Cl.
CPC ....... *A61M 5/326* (2013.01); *A61M 2005/3267* (2013.01); *A61M 2005/3261* (2013.01)
(58) Field of Classification Search
USPC .................................. 604/110, 192, 197, 198
See application file for complete search history.

(56) References Cited

U.S. PATENT DOCUMENTS

| | | | |
|---|---|---|---|
| 7,241,277 B2 * | 7/2007 | Rimlinger et al. | 604/198 |
| 2005/0148943 A1 * | 7/2005 | Chevalier | 604/198 |

FOREIGN PATENT DOCUMENTS

| | | |
|---|---|---|
| WO | 01/30428 A1 | 5/2001 |
| WO | 2005/030301 A1 | 4/2005 |

* cited by examiner

*Primary Examiner* — Nathan R Price
(74) *Attorney, Agent, or Firm* — The Webb Law Firm

(57) ABSTRACT

The invention relates to a sleeve for an injection device comprising a container having an outer flange, said sleeve being provided with one inner radial projection intended to prevent the proximal movement of said outer flange with respect to said sleeve once said container is received within said sleeve, said sleeve being further provided with one inner longitudinal projection extending distally from said inner radial projection and intended to limit the radial movement of said outer flange, said inner radial projection and inner longitudinal projection being provided on a longitudinal leg connected to said sleeve by a deformable bridge allowing radial deflection of said longitudinal leg outwardly when a distal pressure is exerted on said inner radial projection, and inwardly when a proximal pressure is exerted on said inner radial projection. The invention also pertains to an injection device comprising such a sleeve.

10 Claims, 2 Drawing Sheets

SUPPORTING SLEEVE FOR A CONTAINER WITH A FLANGE

The present invention relates to a supporting sleeve intended to receive part of an injection device, such as a container or a syringe body. The invention also relates to a safety device comprising such a supporting sleeve. The invention also relates to an injection device comprising such a supporting sleeve.

In the present application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection. The term "inwardly" means towards the sleeve longitudinal axis, as opposed to the term "outwardly".

An injection device typically comprises a container intended to carry a product to be injected: such a container is generally intended to receive a needle at its distal end, and is usually provided with an outer flange at its proximal end. This outer flange generally provides bearing surfaces for the fingers of the user at the time of injection.

In order to simplify the manufacturing and filling processes of injection devices, the containers or syringe bodies are usually handled and for example filled with a product in a first step. They may be provided as such to a user. Nevertheless, they may also need to be provided with additional parts, which may for example bear safety systems, for example in order to avoid needlestick injuries either before or after use. These additional parts are usually under the shape of sleeves or rings having a longitudinal axis, for example support sleeves which are installed and mounted on the container before use. These sleeves are usually snapfitted on the container, by means of fixing means grasping the outer flange of the container.

Preferably, in particular to ensure a safe injection step, these sleeves should be securely fitted on the container, and their movement, with respect to said container, during all the steps for administering the product, should be prevented.

Such sleeves, provided with inner radial projections, intended to prevent the proximal movement of the flange, and thus of the container, once the sleeve is installed on the container, have been described, for example in WO2005/030301.

Nevertheless, the arrangement of such sleeves is not totally satisfactory as it is still possible to withdraw the container from the sleeve, even once the sleeve is installed on the container, by pulling on the container in the proximal direction with sufficient force for overcoming the resistance opposed by the inner radial projections.

An injection device provided with such a sleeve of the prior art is shown on FIG. 1. This FIG. 1 shows a schematic longitudinal cross section view of an injection device 100 of the prior art comprising a container 1, such as a syringe body, carrying a product 6, provided at its proximal end with an outer flange 2. On the schematic view of FIG. 1, a sleeve 8 is mounted on the container 1. The sleeve 8 and the container 1 have the same longitudinal axis A. The sleeve 8 may be a simple sleeve, allowing to handle the container 1 more easily. On the example shown on FIG. 1, the sleeve 8 is part of a safety system 3 further including a helical spring 7 coupling the sleeve 8 to a tubular body 9. Examples of alternative sleeves included in safety systems are described for example in WO2005/030301.

As shown on FIG. 1, the sleeve 8 of the prior art comprises at its proximal end proximal tabs 4 provided with inner rims 5. The tabs 4 of the sleeve 8 of the prior art are able to be deflected outwardly and radially, as shown with arrows F: this allows to mount the sleeve 8 on the container 1 as follows. The container 1 is provided on its own: it is then introduced in the sleeve 8 by the proximal end of the sleeve 8. During this operation, when the outer flange 2 of the container 1 comes in contact with the inner rims 5, the proximal tabs 4 deflect outwardly and radially, and the outer flange 2 is snapfitted in the sleeve 8.

The inner rims 5 are intended to prevent the container 1 to move proximally with respect to the sleeve 8 once the sleeve 8 is mounted on the container 1, as shown on FIG. 1. Nevertheless, with the sleeve 8 of the prior art, as shown on FIG. 1, it is quite easy to pull proximally on the container 1 and to overcome the resistance of the inner rims 5 and deflect the tabs 4 radially outwardly so as to separate the container 1 from the sleeve 8. This may cause problems: in the example shown, that means that the container 1 is no more provided with the safety system 3 in order to prevent needlestick injuries.

There is therefore a need for a sleeve intended to support and receive at least partially an injection device comprising a container provided at its proximal end with at least one outer flange, which would not allow a person to withdraw the container from the sleeve once the sleeve is installed on the container. In particular, there is a need for such a sleeve that would reinforce the fixing of the container to the sleeve when one would try to pull on the container in the proximal direction, once the sleeve is installed on the container.

A first aspect of the present invention is a sleeve having a longitudinal axis A intended to be mounted on a container of an injection device, said container being provided at its proximal end with at least one outer flange, said sleeve comprising at least one outer body, said sleeve being provided with at least one inner radial projection intended to prevent the proximal movement of said outer flange with respect to said sleeve once said sleeve is mounted on said container, characterized in that said sleeve is further provided with at least one inner longitudinal projection extending distally from said inner radial projection and intended to limit the radial movement of said outer flange with respect to said sleeve, said inner radial projection and inner longitudinal projection being provided on at least one longitudinal leg connected to said outer body by a deformable bridge, said deformable bridge being capable of being deformed with respect to said outer body to allow radial deflection of said longitudinal leg outwardly when a distal pressure is exerted on said inner radial projection, and inwardly when a proximal pressure is exerted on said inner radial projection.

The sleeve of the invention makes it possible to ensure that the container may not be withdrawn from the sleeve once the sleeve is installed or mounted on the container. In particular, because the longitudinal leg of the sleeve of the invention is able to deflect inwardly and radially with respect to said deformable bridge when a proximal pressure is exerted on the inner radial projection, if a person tries to pull on the container in the proximal direction in an attempt to separate the container from the sleeve, the proximal force which is by consequence exerted on the inner radial projection causes the longitudinal leg to deflect inwardly and radially, thereby reinforcing the locking of the container in the sleeve, by means of the outer flange of the container being in proximal and radial abutment against the inner radial projection and the inner longitudinal projection, when the sleeve is mounted on the container.

The deformable bridge is preferably located proximally from said inner radial projection and said inner longitudinal projection. This causes the locking of the container in the sleeve to be reinforced proportionally to the force that may be exerted to try to pull proximally the container out from the sleeve.

In an embodiment of the sleeve of the invention, said longitudinal leg has a free distal end.

In another embodiment of the sleeve of the invention, the deformable ,bridge forms a U turn defining a gap between said longitudinal leg and said outer body. Such an embodiment allows the longitudinal leg to be deflectable on a large amplitude, thereby allowing the sleeve of the invention to be used with containers having various sizes of outer flanges.

In an embodiment of the sleeve of the invention, the inner radial projection has an angled proximal face, directed inwardly and distally, said longitudinal leg being capable of being deflected radially and outwardly when a distal pressure is exerted on said angled proximal face.

In an embodiment of the sleeve of the invention, the inner radial projection has a radial distal face able to abut against said outer flange.

Another aspect of the present invention is a safety device intended to be mounted on a container of an injection device, said container being provided at its proximal end with at least one outer flange, said safety device comprising at least one holder intended to receive at least partly said container, characterized in that said safety device further comprises a sleeve as described above, said sleeve being coupled to said holder by means of at least one biasing member. For example, in a storage position of the safety device, the biasing member is in a stressed state and it tends to urge said sleeve and said holder apart from each other.

A further aspect of the present invention is an injection device comprising a container for carrying a product to be injected, said container being provided at its proximal end with at least one outer flange, characterized in that said injection device further includes a sleeve as described above, said inner radial projection and said inner longitudinal projection being arranged to limit the movement of said container in regards to said sleeve when said sleeve is mounted on said container, proximally by the abutment of said outer flange against said inner radial projection, and radially by the abutment of said outer flange against said inner longitudinal projection.

The sleeve, safety device and injection device of the invention will now be further described in reference to the following description and attached drawings in which.

Figure 1:
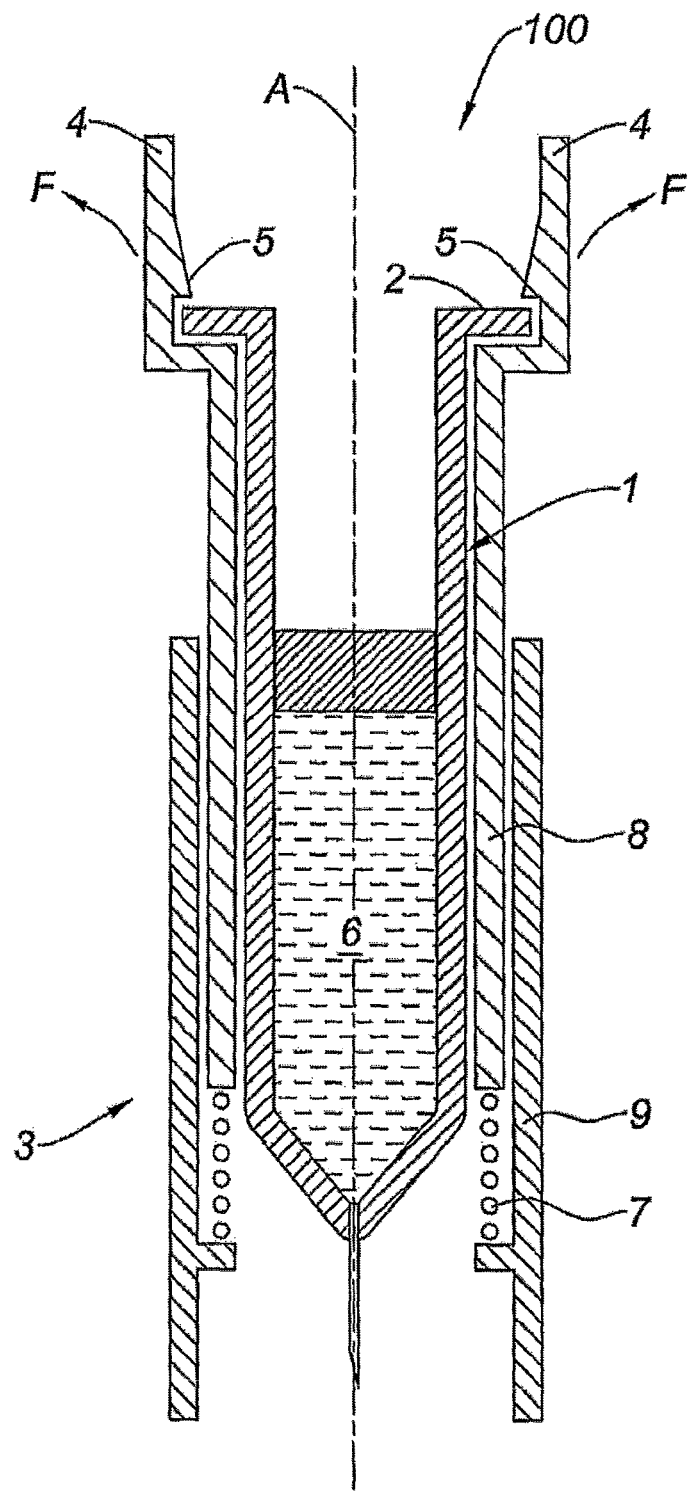
FIG. 1 is a schematic view of a container and a sleeve of the prior art.
Figure 2:
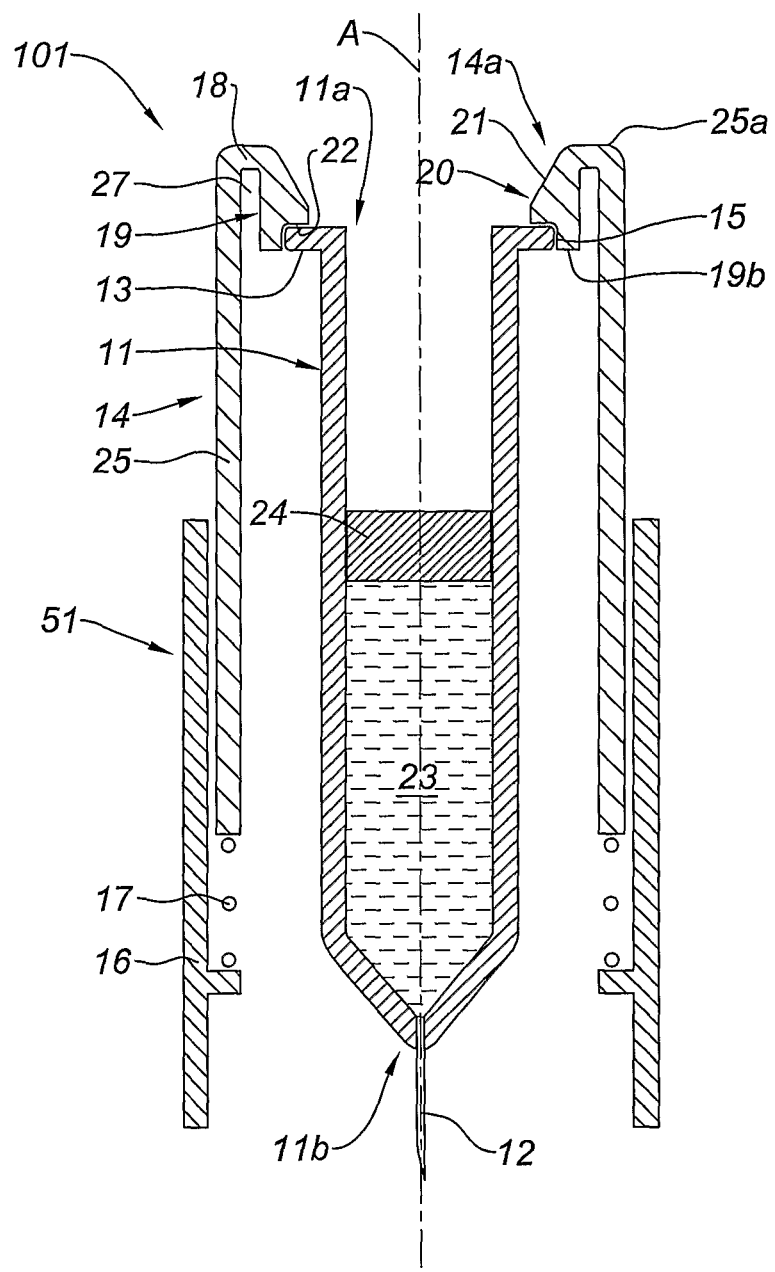
FIG. 2 is a partial sectional view of a sleeve of the invention installed in a safety device assembled with a container of an injection device.

Referring now to FIG. 2, the present invention will now be described in detail.

On FIG. 2 is shown an injection device 101 of the invention comprising a safety device 51 provided with a sleeve 14 of the invention.

The injection device 101 has a longitudinal axis A and comprises a container 11, intended to carry a product 23 to be injected. The container 11 comprises an open proximal end 11a and a substantially closed distal end 11b provided with a needle 12. The proximal end 11a of the container 11 is provided with an outer flange 13. A piston 24 is lodged within the container 11, to form a proximal closure for said product 23.

In another embodiment not shown, the proximal end of the container roughly defines a cylindrical tube and the outer flange is integrated in this cylindrical tube and does not protrude outwardly.

The container 11 is received within an automatic safety device 51. The automatic safety device 51 and the container 11 have the same longitudinal axis A as the injection device 101. On the example shown, the automatic safety device 51 includes two tubular bodies, a sleeve 14 and a holder 16, intended to receive the container 11. The sleeve 14 and the holder 16 are coupled to each other by a biasing member, a helical spring 17 on the example shown, and by other linking means not shown, described for example in WO2005/030301. In a storage or before use position of the safety device, as shown on FIG. 2, the helical spring 17 is in a stressed state and it tends to urge said sleeve 14 and said holder 16 apart from each other.

The automatic safety device 51 of the embodiment shown on FIG. 2 therefore forms a safety system for preventing needlestick injuries, the holder 16 being automatically deployed over the needle 12 by means of the helical spring 17 going back to its rest position at the end of injection : indeed, the injection device 101 is shown on FIG. 2 in a before use position. In this before use position, the holder 16 covers the needle 12. To proceed to the injection, the user grasps the injection device 101 by the sleeve 14, applies the injection device 101 on the injection site (not shown) and pushes distally on the sleeve 14 so as to insert the needle 12 in the injection site, thereby compressing the helical spring 17 between the holder 16 and the sleeve 14. The user then pushes the piston 24 distally with a plunger rod (not shown). At the end of injection, the user releases the pressure on the sleeve 14, the spring 17 comes back to its rest state and the holder 16 covers the needle 12 thereby preventing needlestick injuries.

In other embodiments not shown, the automatic safety device 51 may show various arrangements for forming the safety system. Examples of such sleeves are described in WO200/030301. In further embodiments of the invention, the injection device 101 does not bear a safety device 51 and may simply comprise a sleeve 14 working as a support element receiving the container 11.

With reference to FIG. 2, the sleeve 14 of the invention comprises an outer body 25 provided at its proximal end 25a with longitudinal legs 19 extending in the distal direction. The sleeve 14 can comprise a unique longitudinal leg 19 forming a ring or multiple longitudinal legs 19 spaced from each other and for example regularly distributed on the periphery of the outer body 25. The proximal end 25a of the outer body 25 and the longitudinal leg 19 are connected by a deformable bridge 18 forming a U-turn. In the example shown, each longitudinal leg 19 is provided with a free distal end 19b. The deformable bridge 18 allows the longitudinal leg 19 to be deflectable radially both in the inward direction and in the outward direction, as will appear more clearly from the description below. The U turn delimits a gap 27 located between the longitudinal leg 19 and the outer body 25 that allows the longitudinal leg 19 to be deflectable on a large amplitude.

In another embodiment not shown, the longitudinal leg is not provided with a free end as shown on FIG. 2 but linked to the outer sleeve by a connecting bridge that may be breakable and/or deformable. In both cases, upon proximal pressure applied by the outer flange of the container on the longitudinal leg, the connecting resistance applied by the connecting bridge against the radial deflection of the longitudinal leg is smaller than the deformation resistance applied by the deformable bridge against the same radial deflection of the longitudinal leg. This causes the deformable bridge to better resist to proximal pressure than the connecting bridge: as a consequence, in such a case, upon proximal pressure exerted on the longitudinal leg, the connecting bridge may break or deform, allowing the longitudinal leg to deflect inwardly around the deformable bridge.

Each longitudinal leg 19 is provided with an inner radial projection 20 extending in the inward direction. Each inner radial projection 20 has an angled proximal face 21, directed inwardly and distally, and a radial distal face 22 defining a proximal abutment to the outer flange 13 of the container 11. Each longitudinal leg 19 is also provided with an inner longitudinal projection 15 extending distally from the inner radial projection 20 and defining lateral abutment to the outer flange 13.

As a consequence, during the step of installing the sleeve 14 on the container 11, the container 11 is introduced into the sleeve 14 by the proximal end 14a of the sleeve 14. The outer flange 13 of the container 11 comes in contact with the angled proximal faces 21 of the inner radial projections 20, thereby exerting a distal pressure on said inner radial projections 20. Thanks to the flexibility of the deformable bridge 18 as explained above and of the gap 27, the longitudinal leg 19 is capable of being radially and outwardly elastically deflected, thereby allowing the passage of the flange 13 and thus of the container 11 which is then snapfitted in the sleeve 14. The radial displacement of the container 11 in regards to the sleeve 14 is limited by the abutment of the outer flange 13 against the inner longitudinal projection 15.

The sleeve 14 further comprises distal stops (not shown) for preventing the distal movement of the container 11 with respect to the sleeve 14 before use. Examples of such distal stops, which may be overcome at the time of use of the injection device 101 are described in WO2005/030301.

As appears from FIG. 2, once the sleeve 14 is installed on the container 11, if a person tries to withdraw the container 11 from the sleeve 14 and pulls proximally on the container 11, then the outer flange 13 comes in contact with the radial distal faces 22 of the inner radial projections 20 and therefore exert a proximal pressure on said inner radial projections 20. The deformable bridge 18 being provided proximally from the inner radial projection 20, thanks to the flexibility of the deformable bridge 18, the longitudinal leg 19 is capable of being radially and inwardly deflected. Then, the inner longitudinal projection 15 abuts against the outer flange 13, thereby reinforcing the locking of the outer flange 13, and thus of the container 11, in the proximal direction.

As a consequence, the sleeve 14 of the invention makes it impossible to separate the container 11 from the sleeve 14, once said sleeve 14 has been mounted on the container 11. The sleeve 14 is therefore securely fixed on the container 11. In the example where the sleeve 14 bears a safety device, as shown on FIG. 2, it means that the safety system may not be removed from the injection device 101. The injection device 101 is therefore safer.

Moreover, because the longitudinal legs 19 of the sleeve 14 of the invention are allowed to be deflected radially both in the inward and in the outward direction, the sleeve 14 of the invention may be universally used, for example with containers 11 having various sizes of outer flanges.

The invention claimed is:

1. Sleeve having a longitudinal axis (A) intended to be mounted on a container of an injection device, said container being provided at its proximal end with at least one outer flange, said sleeve comprising at least one outer body, said sleeve being provided with at least one inner radial projection intended to prevent the proximal movement of said outer flange with respect to said sleeve once said sleeve is mounted on said container, characterized in that said sleeve is further provided with at least one inner longitudinal projection extending distally from said inner radial projection and intended to limit the radial movement of said outer flange with respect to said sleeve, said inner radial projection and inner longitudinal projection being provided on at least one longitudinal leg connected to said outer body by a deformable bridge, said deformable bridge being capable of being deformed with respect to said outer body to allow radial deflection of said longitudinal leg, outwardly when a distal pressure is exerted on said inner radial projection, and inwardly when a proximal pressure is exerted on said inner radial projection, wherein said deformable bridge is located proximally from said inner radial projection and said inner longitudinal projection.

2. Sleeve according to claim 1, wherein said longitudinal leg has a free distal end.

3. Sleeve according to claim 1, wherein said deformable bridge forms a U turn defining a gap between said longitudinal leg and said outer body.

4. Sleeve according to claim 1, wherein said inner radial projection has an angled proximal face, directed inwardly and distally, said longitudinal leg being capable of being deflected radially and outwardly when a distal pressure is exerted on said angled proximal face.

5. Sleeve according to claim 1, wherein said inner radial projection has a radial distal face able to abut against said outer flange.

6. Safety device intended to be mounted on a container of an injection device, said container being provided at its proximal end with at least one outer flange, said safety device comprising at least one holder intended to receive at least partly said container, characterized in that said safety device further comprises a sleeve according to claim 1, said sleeve being coupled to said holder by at least one biasing member.

7. Injection device comprising a container for carrying a product to be injected, said container being provided at its proximal end with at least one outer flange, characterized in that said injection device further includes a sleeve according to claim 1, said inner radial projection and said inner longitudinal projection being arranged to limit the movement of said container in regards to said sleeve when said sleeve is mounted on said container, proximally by the abutment of said outer flange against said inner radial projection and radially by the abutment of said outer flange against said inner longitudinal projection.

8. Sleeve according to claim 1, wherein movement of the container with respect to the sleeve is prevented during administration of an injection using the injection device and after completion of the injection using the injection device.

9. Sleeve having a longitudinal axis (A) intended to be mounted on a container of an injection device, said container being provided at its proximal end with at least one outer flange, said sleeve comprising at least one outer body, said sleeve being provided with at least one inner radial projection intended to prevent the proximal movement of said outer flange with respect to said sleeve once said sleeve is mounted on said container, characterized in that said sleeve is further provided with at least one inner longitudinal projection extending distally from said inner radial projection and intended to limit the radial movement of said outer flange with respect to said sleeve, said inner radial projection and inner longitudinal projection being provided on at least one longitudinal leg connected to said outer body by a deformable bridge, said deformable bridge being capable of being deformed with respect to said outer body to allow radial deflection of said longitudinal leg, outwardly when a distal pressure is exerted on said inner radial projection, and inwardly when a proximal pressure is exerted on said inner radial projection, wherein said at least one longitudinal leg has a free distal end.

10. Sleeve having a longitudinal axis (A) intended to be mounted on a container of an injection device, said container being provided at its proximal end with at least one outer flange, said sleeve comprising at least one outer body, said sleeve being provided with at least one inner radial projection intended to prevent the proximal movement of said outer flange with respect to said sleeve once said sleeve is mounted on said container, characterized in that said sleeve is further provided with at least one inner longitudinal projection extending distally from said inner radial projection and intended to limit the radial movement of said outer flange with respect to said sleeve, said inner radial projection and inner longitudinal projection being provided on at least one longitudinal leg connected to said outer body by a deformable bridge, said deformable bridge being capable of being deformed with respect to said outer body to allow radial deflection of said longitudinal leg, outwardly when a distal pressure is exerted on said inner radial projection, and inwardly when a proximal pressure is exerted on said inner radial projection, wherein movement of the container with respect to the sleeve is prevented during administration of an injection using the injection device and after completion of the injection using the injection device.

* * * * *